United States Patent [19]

Jabs

[11] Patent Number: 4,697,461
[45] Date of Patent: Oct. 6, 1987

[54] METHOD AND APPARATUS FOR VERIFYING THE SEISMIC INTEGRITY OF AN ELECTRONIC COMPONENT

[75] Inventor: Robert H. Jabs, Greensburg, Pa.

[73] Assignee: Westinghouse Electric Corp., Pittsburgh, Pa.

[21] Appl. No.: 864,617

[22] Filed: May 19, 1986

[51] Int. Cl.⁴ .................... G01N 3/08; G01N 19/04
[52] U.S. Cl. .................................. 73/862.53; 73/827
[58] Field of Search ........... 73/862.53, 862.01, 150 A, 73/805, 806, 826, 827, 828, 842

[56] References Cited

U.S. PATENT DOCUMENTS

| | | |
|---|---|---|
| 3,564,911 | 2/1971 | Slemmons et al. . |
| 3,572,108 | 3/1971 | McShane et al. . |
| 3,945,248 | 3/1976 | West . |
| 4,213,556 | 7/1980 | Persson et al. . |
| 4,235,114 | 11/1980 | Mohler . |
| 4,282,759 | 8/1981 | Merrell . |
| 4,292,852 | 10/1981 | Morris . |
| 4,453,414 | 6/1984 | Ronemus et al. . |

Primary Examiner—Charles A. Ruehl
Attorney, Agent, or Firm—Daniel C. Abeles

[57] ABSTRACT

A method and apparatus for verifying the seismic integrity of a lead of an electronic component contained in an electric circuit wherein: a force of a desired magnitude is applied to the lead of the electronic component with the magnitude corresponding to the expected maximum force which would be exerted on the lead by an earthquake, and an indication is provided when the lead has been subjected to the applied force for a given period of time corresponding to the approximate period of time the maximum force of an earthquake would be exerted on the lead. Moreover, the force is released if the desired magnitude has been applied for a further preset period of time which is greater than the given period of time, or if the magnitude of the applied force exceeds a preset maximum value.

20 Claims, 4 Drawing Figures

METHOD AND APPARATUS FOR VERIFYING THE SEISMIC INTEGRITY OF AN ELECTRONIC COMPONENT

BACKGROUND OF THE INVENTION

The present invention relates to a method and apparatus for verifying the seismic integrity of leads of an electronic component. More specifically, the present invention relates to a method and apparatus which can be utilized to determine whether or not certain aged electrical components, i.e., components which have been installed in an electrical circuit for a number of years, have sufficient lead integrity to withstand a seismic event, particularly such electrical components which have been installed in nuclear power plants.

The aging of electronic components, i.e., resistors, capacitors, etc. and the effect of such aging on the integrity of the component during a seismic event, i.e., an earthquake, has not been well studied to date. However, the aging of electronic components, and the integrity of same, is of significant importance to safety systems installed in various type plants, particularly nuclear power plants, because an aging mechanism must not degrade an electronic component to a point where a common mode failure of redundant systems can occur during an earthquake.

As a result of the tests conducted to determine if aged electrical or electronic components will maintain their electrical integrity when subjected to seismic stresses, component lead failure is a predominant failure mode observed in those few components not capable of potentially surviving a seismic event. That is, it has been found that one of the recurring failure modes given for components subjected to seismic stress is the separation of the lead from the component body. Moreover, it appears that this lead failure appears to be isolated to individual specific components, and not generic to any family of components. Consequently, there is a problem in determining just how to detect such component lead failure, particularly with regard to components which are already installed in operating systems.

One way to detect component lead failure is to seismically test equipment which has been installed in an operating system, particularly in a nuclear power plant, for say ten years. This manner of testing, however, is not practical, because such testing can deteriorate the equipment to where its ability or capability to withstand any further earthquake induced force is questionable. A further testing alternative is to periodically conduct accelerating aging and seismic testing on a wide range of electronic components so as to attempt to detect this lead integrity failure phenomenon in advance. However, the results gathered by such a testing program would clearly not apply to equipment which uses components procured and installed several years before. Consequently, it appears that in order to test the lead integrity of components already installed, it is necessary to periodically check the component leads with a meaningful test which will determine their integrity.

SUMMARY OF THE INVENTION

It is therefore the object of this invention to provide a method and apparatus which is capable of testing the seismic integrity of the leads of electrical components which are already installed in a circuit of an operating system without requiring that the components be removed for testing.

It is a further object of the present invention to provide a method and apparatus for verifying the seismic integrity of the leads of aged electronic components which does not subject the components to overstresses which may cause same to subsequently fail.

The above objects are achieved by an apparatus for verifying the seismic integrity of a lead of an electronic component contained in a circuit which, according to the invention, comprises: first means for applying a force to a lead of an electronic component which is connected in a circuit and for producing a first output signal corresponding to the magnitude of the applied force; a second means, responsive to the first output signal, for providing a second output signal when the magnitude of the force is at a desired preset value; and a third means, responsive to the second output signal, for providing an indication when the second output signal is present for a preset desired period of time.

Preferably the preset value corresponds to the maximum expected force to be exerted on the lead by an earthquake and the preset period of time corresponds to the expected duration of such maximum force.

According to a preferred feature according to the invention, the apparatus further includes a fourth means, responsive to the first output signal and connected to the first means, for causing a force being applied by the first means to be released if the applied force exceeds a preset maximum value; and fifth means, responsive to the second output signal, for causing a force being applied by the first means to be released when the second output signal is present for a further preset period of time after the desired period of time.

According to the disclosed preferred embodiment of the invention, the apparatus is a manual apparatus which is hand held, at least in part, and which includes an indicating means responsive to the first output signal for indicating the magnitude of the force being applied by the first means; and wherein: the first means comprises a probe which has a hook at one end so that it is connectable to a lead of an electronic component for applying a force, a load cell, which produces said first output signal, connected to the probe, a housing in which the load cell is disposed, and releasable connection means for normally connecting the load cell and the probe to the housing; and the fourth and the fifth means are each connected to and control the releasable connection means to cause same to disconnect the first means from the housing.

Basically, the preferred embodiment of the method of verifying a seismic integrity of a lead of an electronic component contained in an electric circuit according to the invention comprises:

Applying a force of a desired magnitude to the lead of the electronic component with the magnitude corresponding to the expected maximum force which would be exerted on the lead by an earthquake; and providing an indication when the force has been applied for a given period of time corresponding to the approximate duration the maximum force would be exerted on the lead by an earthquake.

According to preferred features of the method according to the invention, the applied force is released if the desired magitude has been applied for a further preset period of time which is greater than the given period of time; the given period of time is in the range from approximately 2-4 seconds, and the desired magnitude of force is in the range from approximately 2-5 pounds, depending on the component.

DETAILED DESCRIPTION OF THE PREFERRED EMBODIMENT

Figure 1:
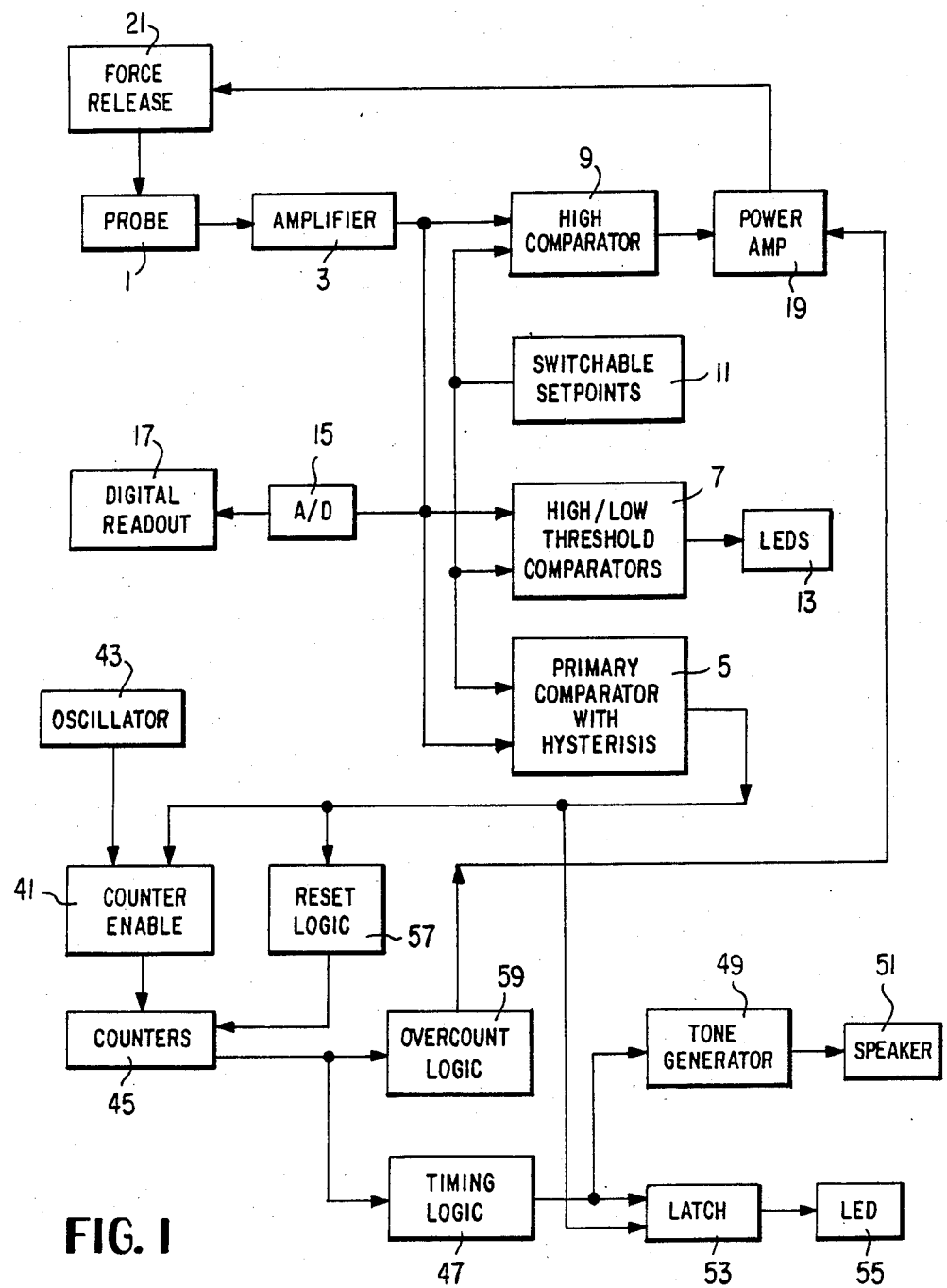
FIG. 1 is block circuit diagram of a preferred embodiment of the apparatus according to the invention for carrying out the method according to the invention.

As shown in FIG. 1, the circuit according to the invention includes a probe 1 for applying a force to a lead of an electrical component, for example, a resistor or a capacitor, which is connected in an electrical circuit, and for providing an electrical output signal corresponding to the applied force. The output signal from the probe 1 is fed, via an amplifier 3, to the signal input of each of a plurality of comparators 5, 7 and 9. The respective reference inputs of the comparators 5, 7 and 9 are supplied with respective selectable and adjustable set point values via a circuit 11, which may for example be a plurality of multi-contact switches, one for each comparator, which are ganged together. Comparator 5, which is provided with hysterisis, is the primary comparator for the test circuit arrangement according to the invention, and consequently its reference input is provided with a set point value corresponding to the force desired to be applied to the component lead by the probe 1, for example, a set point value corresponding to two pounds of force, so that the comparator 5 will produce an output signal only when this desired force is being applied. The high/low threshold comparator 7, which may in fact be realized by separate high and low comparators, is provided in order to aid the operator of the probe in applying the proper desired force to the component lead. Consequently, the high/low threshold comparator 7 is provided with two set point values just above and just below the set point values applied to the comparator 5, for example, values corresponding to 2.5 pounds and 1.5 pounds, respectively, so that the high/low threshold comparator 7 will produce an output signal when the force being applied by the probe 1 exceeds either of these threshold values. The output signals from the comparator 7 are fed to an indicator 13 containing, for example, two light emitting diodes, which indicate whether the force being applied by the probe 1 is above or below the desired force value. Instead of, or in addition to, the comparator 7 and indicators 13, a direct read-out of the force being applied by the probe 1 may be provided by connecting the output of the amplifier 3 via an analog to digital converter 15 to a digital read-out indicator 17.

In order to prevent an excessive force from being applied to the component lead by the probe 1, the high comparator 9 is provided with a set point value corresponding to an excessive force, for example, four pounds with the above indicated set point value for the comparator 5, and produces an output signal when its input signal indicates that the applied force exceeds this excessive force value. The output signal from comparator 9 is fed to a powder amplifier or driver circuit 19 which in turn actuates a circuit arrangement 21 which acts on the probe 1 to cause same to release the force then being applied to a component lead by the probe 1.

Figure 2:
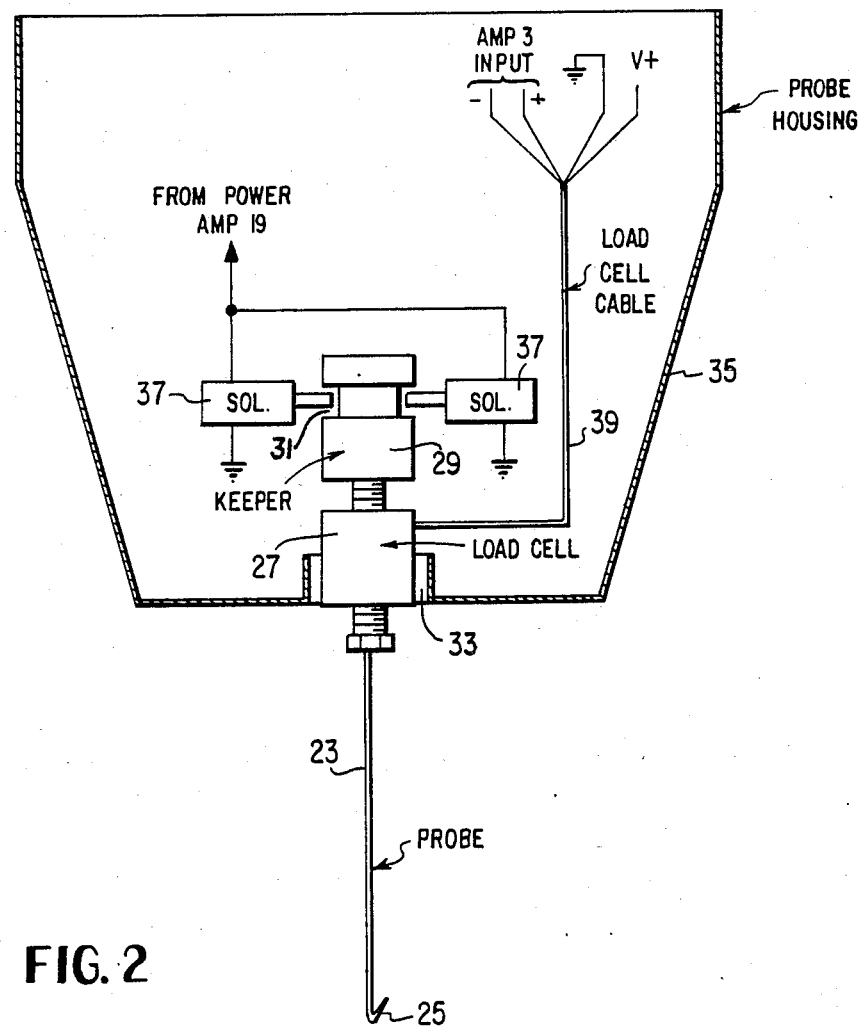
FIG. 2 is a schematic drawing of a preferred embodiment of the force applying and measuring arrangement, i.e., the probe and probe force release mechanism, of the preferred embodiment of the invention shown in FIG. 1.

To provide a clearer understanding of the operation of the circuit of FIG. 1 as thus far described, reference is now made to FIG. 2 which schematically shows a preferred embodiment of a probe 1, which may, for example, be hand held by the operator. As shown in FIG. 2, the probe 1 essentially includes a rod 23 having means for engaging a component lead at one end, for example a hook 25, and its other end threadingly connected to a load cell 27, for example a strain gauge, which produces the input signal for the amplifier 3. Preferably the rod 23 is formed of a suitable insulating material or is constructed such that the end containing the hook 25 is electrically insulated from the end connected to the load cell 27. The opposite end of the load cell 27 is threadingly connected to a keeper 29 which is provided with a circumferential groove 31. The portion of the probe 1 containing the load cell 27 and the keeper 29 is disposed in an opening or bore 33 formed in the end of a probe housing 35 so that it is axially moveable within opening 33. In order to fasten the keeper 29, and thus probe 1, to the housing 35, a pair of solenoids 37 (which in the illustrated embodiment of the probe constitute the force releasing circuit 21 of FIG. 1) are mounted in the housing 35 so that their respective plungers normally engage in the circumferential groove 31 of the keeper 29 when the solenoids 37 are unenergized. Accordingly, with the solenoids 37 in the unenergized position is shown in FIG. 2, a force produced on the lead of an electrical component by engaging same with the hook 25 and then pulling on the probe housing 35, will cause the load cell 27 to provide an output signal corresponding to the applied force, with this output signal being fed to the input of amplifier 3 via the load cell cable 39. Alternatively, when the solenoids 37 are energized by the power amplifier 39, the mechanical connection between the probe 1 and the housing 35 will be released, and consequently the force being exerted on the component lead by the probe hook 25 will also be released.

Returning now to FIG. 1, as indicated above, the primary comparator 5 produces an output signal when the force being applied to a component lead by the probe 1 corresponds to the desired force. In order to test the integrity of the lead, as indicated above it must be determined whether the lead can withstand the desired force for a preset period of time, e.g. three seconds. For this purpose, the output of the primary comparator 5 is connected to the control input of a counter enable or gate circuit 41 which is connected between the output of an oscillator 43 and the input of a counter or counters 45. As long as the primary comparator 5 is producing its output signal indicating that the correct force is being applied by the probe 1, the output pulses from the oscillator 43 will be passed to the counter 45 via the enabler gate circuit 41, causing the counter 45 to continuously count the pulses.

The state of the counter 45 is continuously monitored by a timing logic circuit 47 which produces an output signal whenever the counter 45 reaches a counter state corresponding to the predetermined or preset period of time for a test, e.g. three seconds. The output signal from the timing logic circuit 47 in turn is fed to an indicating device to provide an indication that a test has been completed, i.e. a desired force has been applied to the lead of an electrical component for a desired period of time. As shown in FIG. 1, the output signal from the timing logic circuit 47 is used to actuate both a tone generator 49 to produce an audible indication via a speaker 51, and to activate a latch circuit 53 which will turn on a visual indicator 55 such as a light emitting diode (LED). Preferably, the timing logic circuit 47 produces its output signal for only a short period of time, for example, two seconds, so that the tone generator 49 will only be actuated for this period of time. On the other hand, the latch 53 and consequently the visual indication provided by the indicator 55 will remain actuated until the latch 53 is reset by the absence of an output signal from the primary comparator 5, indicating that the applied force is above or below the threshold level of the primary comparator 5, e.g. has been released.

In order to reset the counter 45 at the end of a test, the output of the primary comparator 5 is also connected via a reset logic circuit 57 to the reset input of the counter 45. Moreover, the reset logic circuit 57 will also automatically reset the counter 45 if, at any time after the primary comparator 5 has been triggered to produce its output signal, the force being applied by the operator of the probe should be lowered to a value below the built-in hysterisis of the primary comparator 5. Consequently, in such case, the reset logic circuit 57 will cause the counter 45 to be automatically reset and the timing cycle to start again from the beginning, thus assuring the accuracy of the test results.

Finally, to ensure that the applied force, i.e., the desired preset force, is not applied to the component lead for an excessive period of time, and thus possibly damage the component lead, the state of the counter 45 is additionally continuously monitored by an overcount logic circuit 59 which will produce an output signal whenever the state of the counter 45 corresponds to a further given period of time which is greater than that used for the test. The output signal from overcount logic circuit 59, which may for example be produced at a counter state corresponding to six seconds, is fed to the power amplifier 19 so as to actuate same and energize the solenoids 37 (FIG. 2) to cause the probe 1 to disengage from the housing 35 and release the force being applied to the component lead.

Figure 3:
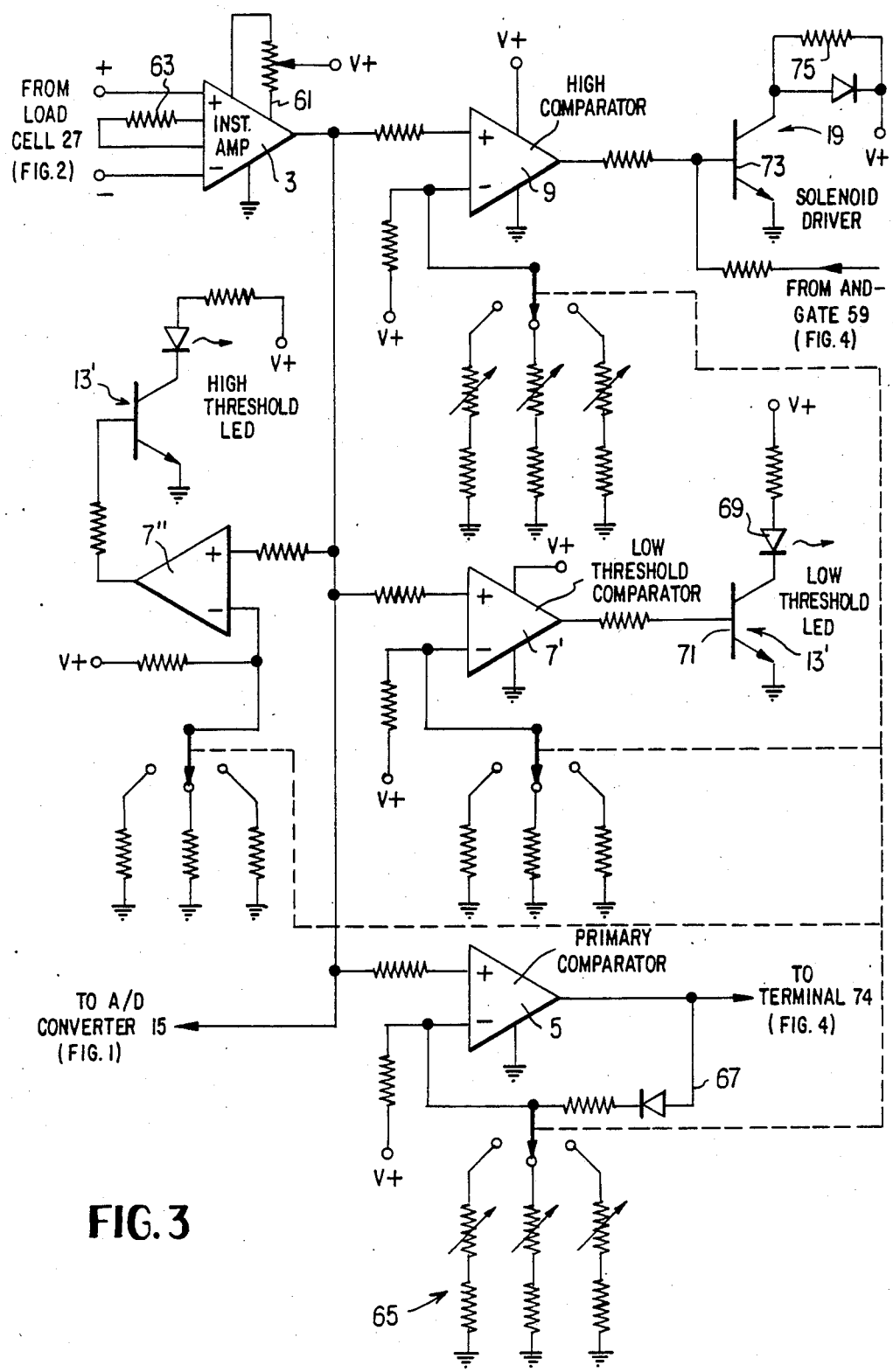
FIGS. 3 and 4, together are a detailed circuit diagram of the preferred embodiment of the invention shown in FIG. 1.
Figure 4:
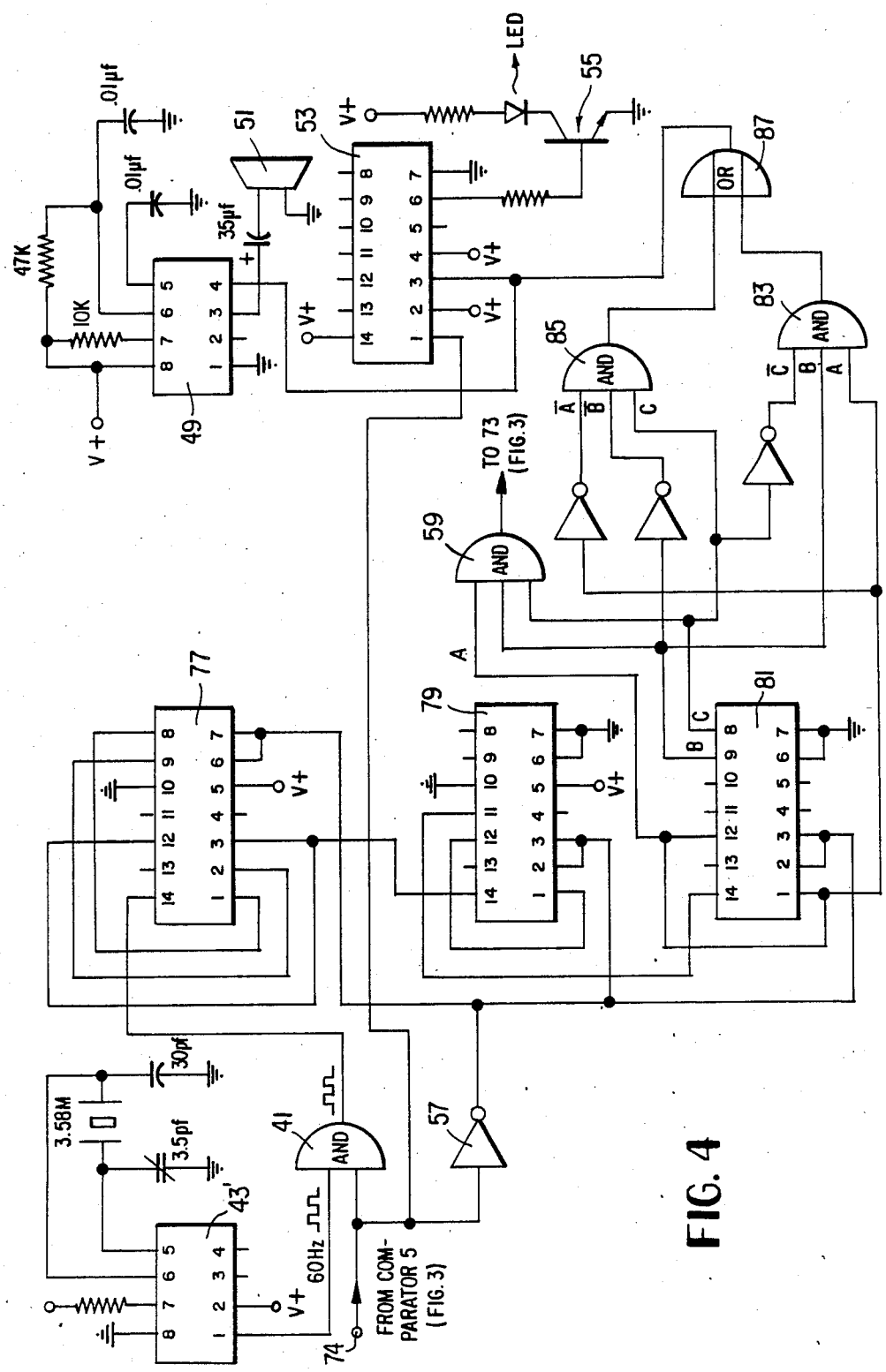

Turning now to FIGS. 3 and 4, which together show a preferred embodiment of a circuit diagram for realizing the circuit shown in block form in FIG. 1, and wherein the same reference numerals are utilized where ever possible to represent the same elements, the signal terminals of the load cell 27 (FIG. 2) are fed to the input of the amplifier 3 which, as shown in FIG. 3, is realized by an operational amplifier. Preferably, as shown, the amplifier 3 is provided with a circuit 61 to enable the zero adjustment of the amplifier, as well as a resistor 63 connected across the input terminals of the amplifier, with the resistor 63 being selected so as to permit scaling of the amplifier 3. As shown, each of the comparators 5, 7 and 9 is likewise realized by a respective operational amplifier, or in the case of the high-low threshold comparator 7, by two operational amplifiers 7' and 7" for the low threshold value and for the high threshold value respectively. The operational amplifiers of the respective comparators 5, 7 and 9 each have their positive input connected to the output of the amplifier 3 and their negative input connected to the source of operating voltage V+, which in the illustrated circuit is nine volts. As further shown, the negative input of each of the operational amplifiers forming the comparators 5, 7 and 9 is connected to a respective multiposition switch for example the multiposition switch 65 connected to the primary comparator amplifier 5, so as to provide the desired set points for the various comparators. As indicated, the moveable contents of the respective multiposition switches, which correspond to the block 11 of FIG. 1, are all mechanically connected together so that the corresponding proper desired set point will be supplied to each of the comparators at the same time. As can be seen from FIG. 3, the comparator 5 differs from the remaining comparators in that it has a feedback circuit 67 connected between its output and its negative input in order to provide for the desired hysterisis.

The outputs of the high and low comparators 7" and 7' are each connected to a respective indicator circuit 13', each including a light emitting diode 69 connected in the emitter-collector path of a transistor 71, while the output of the high comparator 9 is connected to the base of a further transistor 73 having its emitter-collector path connected in series with the coils 75 of the solenoids 37 (FIG. 2) across the source of operating potential.

As indicated in FIG. 3, the output of the amplifier 3 may be connected to the analog to digital converter 15 of FIG. 1, in which case the two comparators 7' and 7" as well as their associated indicators may be eliminated if desired.

The output of the primary comparator 5 is connected to one input of an AND-gate (FIG. 4), which constitutes the enable circuit 41 of FIG. 1. The other input of AND-gate 41 is connected to the output, i.e., terminal No. 1, of an integrated circuit 43', for example an integrated circuit MM 5369, which, together with the crystal circuit connected to its terminals Nos. 5 and 6 constitutes the oscillator 43 of FIG. 1, and provides a 60Hz square wave at its output. The output signal from the AND-gate 41 is fed to the count input of the first of three series connected counters 77, 79 and 81 which together constitute the counter 45 of FIG. 1. The three counters 77, 79 and 81 are each realized by a respective integrated circuit, e.g. an integrated circuit number 74C90, which, when connected as indicated in FIG. 4, cause the counter 77 to divide by six and the counter 79 to divide by ten. The three counters 77, 79 and 81 are reset by the inverter 57 connected between the output of comparator 5 (FIG. 3) and the appropriate terminals of the three counter circuits 77, 79, 81.

As shown in FIG. 4, the timing logic circuit 47 of FIG. 1 is formed by a pair of AND-gates 83 and 85, each having three inputs connected to appropriate terminals of the counter 81, and an OR-gate 87 having its inputs connected to the outputs of the AND-gates 83 and 85. With the connections of the AND-gate 83 and 85 to the counter 81 as shown, the OR-gate 87 will produce an output signal when the counter 81 reaches a count corresponding to three seconds and will maintain this output signal for two seconds thereafter. The output signal from the OR-gate 87 is fed to pin No. 4 of an integrated circuit i.e. a tone generator integrated circuit number 555, which constitutes the tone generator 49 of FIG. 1, and whose output pin No. 3 is connected to the speaker 51. The output of the OR-gate 87 is also connected to a further integrated circuit, for example a IC74C74, which constitutes the latch 53 of FIG. 1, and whose output pin No. 6 is connected to a further light emitting diode indicating circuit , i.e., the indicator 55. The reset terminal i.e., pin No. 1, of the integrated circuit forming latch 53 is likewise connected to the output of the comparator 5 (FIG. 3) in order to reset the latch 53 at the appropriate time. Finally, the overcount logic 59 of FIG. 1 is realized by a single AND-gate having three inputs appropriately connected to respective pins of the counter 81 so as to provide an output signal when the counter 81 reaches a count corresponding to six seconds. The output of AND-gate 59 is connected to the base of the transistor 73 (FIG. 3) so as to energize the solenoid coil 75 at the appropriate time.

As can be appreciated, the above described device provides a simple and reliable apparatus for testing the integrity of the leads of electrical components which are already installed in an electrical circuit of an operating system without requiring that the components be removed prior to testing and without subjecting the components to excessive forces. In order to test or verify the seismic integrity of such a component, a force of a desired magnitude corresponding to the expected maximum force which would be exerted on the lead of the component by an earthquake is initially applied to the lead, e.g. by engaging the lead with the hook 25 and exerting a pull on the housing 35 until the desired force is produced and the comparator is triggered. This desired force is then maintained by the operator until an indication is provided, e.g. by one or both of the indicators 51 and 55 showing that the desired applied force has been applied to the component lead for a preset period of time corresponding to the approximate duration of the maximum force of an earthquake. The given or preset period of time for the test is in general in the range of approximately two to four seconds, which is the approximate duration plus margin of the strong motion or maximum force of an earthquake. The desired force to be applied to the component lead will vary to some extent based on the size of the component. However, in general, the desired force will range from approximately two pounds for small components to five pounds for larger components.

After the indication, which verifies the seismic integrity of the component lead, the applied force is removed or released. Of course, if the desired preset force cannot be applied to the lead for the preset period of time, this is an indication that the component would have failed upon the occurrence of an earthquake, and therefore was in need of replacement, which can now be done under safe conditions. To protect the component under test from being subjected to excessive forces which could tend to unnecessarily damage same, the applied force is automatically released if the desired magnitude of force has been applied for a further period of time after the verifying indication has been provided, or if an excessive force is applied at any time during the test procedure.

It will be understood that the above description of the present invention is susceptible to various modifications, changes and adaptations, and the same are intended to be comprehended within the meaning and range of equivalents of the appended claims.

What is claimed is:

1. Apparatus for verifying the seismic integrity of a lead of an electronic component which is connected in a circuit comprising, in combination:

first means for applying a force to a lead of an electronic component which is connected in a circuit and for producing a first output signal corresponding to the magnitude of the applied force; second means, responsive to said first output signal, for providing a second output signal when the magnitude of the applied force is at a desired preset value; and third means, responsive to said second output signal, for providing an indication when said second output signal is present for a preset desired period of time.

2. The apparatus of claim 1 further comprising fourth means, responsive to said first output signal and connected to said first means, for causing a force being applied by said first means to be released if the applied force exceeds a preset maximum value; and fifth means, responsive to said second output signal, for causing a force being applied by said first means to be released when said second output signal is present for a further preset period of time after said desired period of time.

3. The apparatus of claim 2 further comprising means, responsive to said first output signal, for indicating the force being applied by said first means.

4. The apparatus of claim 2 wherein said first means comprises: a force probe including means for engaging a lead of an electronic component to apply a force, and a load cell, which produces said first output signal, connected to said means for engaging to measure the applied force; a housing; and releasable connection means for normally connecting the portion of said probe containing said load cell to said housing; and wherein said fourth and said fifth means are each connected to and control said releasable connection means to cause same to disconnect said probe from said housing.

5. The apparatus of claim 4 wherein: said means for engaging comprises a rod having a hook for engaging a component lead at one end; said load cell is connected to the opposite end of said rod and extends into said housing for axial relative movement; said probe further includes a keeper connected to said load cell for movement therewith; and said releasable connection means includes means, mounted on said housing and responsive to the output signals from said fourth and fifth means, for normally engaging said keeper to prevent axial movement of said load cell relative to said housing.

6. The apparatus of claim 5 wherein: said keeper is provided with a peripheral groove; and said means for normally engaging said keeper comprises at least one solenoid which is disposed adjacent to said keeper and oriented transverse to the longitudinal axis of said keeper so that the plunger of said solenoid normally engages in said groove when said solenoid is not energized.

7. The apparatus of claim 2 wherein: said second means comprises a comparator for comparing said first output signal with a preset reference value corresponding to said desired preset value of magnitude; and said third means comprises a source of timing signals, a counter, means connected between the output of said source and the input of said counter for connecting said source to said counter when said second output signal is present, indicating means for providing an indication, and logic circuit means for providing an output signal to energize said indicating means when said counter reaches a preset counter state corresponding to said preset desired period of time.

8. The apparatus of claim 7 wherein: said indicating means is a sound indicating means.

9. The apparatus of claim 8 wherein said sound indicating means includes a tone generator responsive to said output signal from said logic circuit means, and a speaker connected to the output of said tone generator.

10. The apparatus of claim 7 wherein said logic circuit means includes timing logic for producing its said output signal for only a given period of time.

11. The apparatus of claim 10 further comprising latch circuit means having inputs connected to the outputs of both said comparator and said logic circuit means, said latch circuit means being responsive to said output signal from said logic circuit means for thereafter energizing said indicator for as long as said second output signal is present.

12. The apparatus of claim 7 further comprising reset means for resetting said counter whenever said second output signal is not present.

13. The apparatus of claim 7 wherein said fifth means comprises further logic circuit means, responsive to said counter reaching a further counter state, for providing an output signal to said first means to cause same to release a force being applied.

14. The apparatus of claim 2 wherein said preset magnitude of force and said preset desired period of time correspond respectively to the expected maximum force and duration which would be exerted on the lead by an earth quake.

15. A method of verifying the seismic integrity of a lead of an electronic component contained in an electric circuit comprising the steps of:

applying a force of a desired magnitude to the lead of the electronic component with said magnitude corresponding to the expected maximum force which would be exerted on said lead by an earthquake; and providing an indication when said force has been applied for a given period of time corresponding to the approximate duration said maximum force would be exerted on said lead by an earthquake.

16. The method defined in claim 15 further comprising: releasing said force if said desired magnitude has been applied for a further preset period of time which is greater than said given period of time.

17. The method defined in claim 15 wherein said given period of time is in the range from approximately 2–4 seconds.

18. The method defined in claim 17 wherein said magnitude is in the range from approximately 2–5 pounds.

19. The method defined in claim 15 wherein said circuit containing said component is contained in a nuclear power plant.

20. The method defined in claim 15 wherein said step of applying includes applying a force to said lead, measuring and indicating the value of the applied force, and increasing said force until said predetermined magnitude is indicated; and further comprising automatically releasing said force if the measured value is above a preset maximum value which is greater than said desired value.

* * * * *